United States Patent
Peterson, Jr.

(10) Patent No.: US 12,115,271 B1
(45) Date of Patent: Oct. 15, 2024

(54) INSTANT-ON HANDHELD SANITIZER

(71) Applicant: HEPCO HOLDINGS, LLC, St. Petersburg, FL (US)

(72) Inventor: Daniel J. Peterson, Jr., Lakeland, FL (US)

(73) Assignee: HEPCO HOLDINGS, LLC, St. Petersburg, FL (US)

(*) Notice: Subject to any disclaimer, the term of this patent is extended or adjusted under 35 U.S.C. 154(b) by 76 days.

(21) Appl. No.: 18/187,025

(22) Filed: Mar. 21, 2023

(51) Int. Cl.
*A61L 2/20* (2006.01)
*A61L 2/10* (2006.01)
*A61L 2/26* (2006.01)

(52) U.S. Cl.
CPC ............... *A61L 2/10* (2013.01); *A61L 2/202* (2013.01); *A61L 2/26* (2013.01); *A61L 2202/11* (2013.01); *A61L 2202/14* (2013.01); *A61L 2202/16* (2013.01)

(58) Field of Classification Search
CPC ... A61L 2/10; A61L 2/202; A61L 2/26; A61L 2202/11; A61L 2202/14; A61L 2202/16
USPC ........................................................ 422/105
See application file for complete search history.

(56) References Cited

U.S. PATENT DOCUMENTS

| | | | |
|---|---|---|---|
| 2,569,079 | A | 10/1950 | Special |
| 3,662,175 | A | 5/1972 | Davidson |
| 5,446,289 | A | 8/1995 | Shodeen et al. |
| 6,146,588 | A | 11/2000 | Deighton |
| 7,090,649 | B2 | 8/2006 | Kang |
| 7,344,272 | B2 | 3/2008 | Cooper et al. |
| 7,875,869 | B1 | 1/2011 | Shadan |
| 7,960,706 | B2 | 6/2011 | Ullman |
| 8,241,565 | B1 | 8/2012 | Abdul |
| 8,624,202 | B2 | 1/2014 | Gil et al. |

(Continued)

FOREIGN PATENT DOCUMENTS

| | | | |
|---|---|---|---|
| CN | 213354249 U | * | 6/2021 |
| EP | 2295112 A1 | | 3/2021 |

(Continued)

OTHER PUBLICATIONS

CN-213354249 U (Year: 2024).*

(Continued)

*Primary Examiner* — Huy Tram Nguyen
(74) *Attorney, Agent, or Firm* — Larson & Larson; Frank Liebenow; Justin P. Miller

(57) ABSTRACT

A handheld sanitization device includes ultraviolet emitter(s) housed within an enclosure. The enclosure has a window for passing the ultraviolet light from the ultraviolet emitter(s). A mechanism selectively blocks the window that has an open position in which the ultraviolet light passes through the window and out of the enclosure and has a closed position in which the window is occluded, thereby blocking the passage of the ultraviolet light from the ultraviolet emitter(s), through the window. The mechanism is biased into the closed position. There is an electromechanical device physically interfaced between the enclosure and the mechanism and there is a trigger switch electrically coupled to the electromechanical device. Responsive to operation of the trigger switch, the mechanism is moved from the closed position into the open position by movement of the electromechanical device, thereby, releasing the ultraviolet light through the window.

20 Claims, 11 Drawing Sheets

(56) References Cited

U.S. PATENT DOCUMENTS

| | | |
|---|---|---|
| 8,784,731 B2 | 7/2014 | Gil et al. |
| 9,114,183 B2 | 8/2015 | Campagna |
| 10,596,280 B1 | 3/2020 | Henderson |
| 11,033,646 B1 | 6/2021 | Mckeon |
| 2001/0042842 A1 | 11/2001 | Leighley |
| 2003/0030015 A1 | 2/2003 | Waluszko |
| 2003/0088297 A1 | 5/2003 | Stoppler |
| 2003/0153962 A1 | 8/2003 | Cumbie |
| 2003/0163068 A1 | 8/2003 | Kang |
| 2004/0052702 A1 | 3/2004 | Shuman |
| 2004/0116984 A1 | 6/2004 | Spooner |
| 2004/0256581 A1* | 12/2004 | Au .............. A61L 2/10 250/504 H |
| 2004/0262241 A1 | 12/2004 | Socha |
| 2005/0013729 A1 | 1/2005 | Brown-Skrobot |
| 2005/0263015 A1 | 12/2005 | Mulgrew |
| 2006/0047329 A1 | 3/2006 | Krespi |
| 2006/0089687 A1 | 4/2006 | Spooner |
| 2006/0206173 A1 | 9/2006 | Gertner |
| 2007/0075268 A1 | 4/2007 | Harris |
| 2007/0092832 A1 | 4/2007 | Grossman |
| 2007/0164232 A1 | 7/2007 | Rolleri et al. |
| 2007/0185553 A1 | 8/2007 | Kennedy |
| 2007/0192986 A1 | 8/2007 | Garcia et al. |
| 2007/0208395 A1 | 9/2007 | Leclerc et al. |
| 2007/0274879 A1 | 11/2007 | Millikin |
| 2008/0103560 A1 | 5/2008 | Powell |
| 2008/0172113 A1 | 7/2008 | Gourgouliatos |
| 2008/0208297 A1 | 8/2008 | Gertner |
| 2008/0234786 A1 | 9/2008 | Cumbie |
| 2008/0294227 A1 | 11/2008 | Perez |
| 2008/0308748 A1 | 12/2008 | Burrows |
| 2008/0310996 A1 | 12/2008 | Kim |
| 2009/0065716 A1 | 3/2009 | Ullman |
| 2009/0143842 A1 | 6/2009 | Cumbie |
| 2009/0169426 A9 | 7/2009 | Toepfer et al. |
| 2009/0240310 A1 | 9/2009 | Kennedy |
| 2010/0049177 A1 | 2/2010 | Boone, III |
| 2010/0076526 A1 | 3/2010 | Krespi |
| 2010/0104470 A1 | 4/2010 | McCabe |
| 2010/0179469 A1 | 7/2010 | Hammond |
| 2011/0037002 A1 | 2/2011 | Johnson |
| 2011/0240883 A1 | 10/2011 | Ullman |
| 2012/0045363 A1 | 2/2012 | Gil |
| 2012/0310141 A1 | 12/2012 | Kornfield |
| 2012/0328474 A1 | 12/2012 | Campagna |
| 2013/0101461 A1 | 4/2013 | Gil et al. |
| 2013/0336839 A1 | 12/2013 | Gil |
| 2014/0170019 A1 | 6/2014 | Gil |
| 2014/0222117 A1 | 8/2014 | Bourke, Jr. |
| 2014/0264076 A1 | 9/2014 | Bettles |
| 2014/0277299 A1 | 9/2014 | Intintoli |
| 2014/0305470 A1 | 10/2014 | Desu-Kalyanam |
| 2015/0037201 A1 | 2/2015 | Armour |
| 2015/0238774 A1 | 8/2015 | Anderson |
| 2015/0290346 A1 | 10/2015 | Kassel |
| 2015/0359668 A1 | 12/2015 | Kornfield |
| 2016/0101202 A1 | 4/2016 | Gil |
| 2016/0114067 A1 | 4/2016 | Dobrinsky |
| 2016/0129279 A1 | 5/2016 | Ferolito |
| 2016/0158575 A1 | 6/2016 | Levatter |
| 2016/0175550 A1 | 6/2016 | Taylor |
| 2016/0287896 A1 | 10/2016 | Anderson |
| 2018/0055960 A1 | 3/2018 | Reiber |
| 2018/0322753 A1 | 11/2018 | Stibich |
| 2019/0060495 A1 | 2/2019 | Gil |
| 2019/0262487 A1 | 8/2019 | Gil |
| 2021/0316024 A1 | 10/2021 | Green |
| 2021/0330827 A1 | 10/2021 | Lucio |
| 2022/0047738 A1 | 2/2022 | Shah |
| 2022/0226519 A1 | 7/2022 | Kudo |
| 2022/0313850 A1 | 10/2022 | Baarman |

FOREIGN PATENT DOCUMENTS

| | | |
|---|---|---|
| WO | WO2016179705 A1 | 11/2016 |
| WO | 2022139699 | 6/2022 |

OTHER PUBLICATIONS

Tianhong Dai et al., Ultraviolet C irradiation: an alternative antimicrobial approach to localized infections? Feb. 10, 2012.

Boker, A., G. Rolz-Cruz, B. Cumbie, and A. Kimball. 2007. A single-center, prospective, open-label, pilot study of the safety, local tolerability, and efficacy of ultraviolet-C (UVC) phototherapy for the . . . Centers for Disease Control and Prevention.

Jesse Miller, Efficacy of an Ozone-Generating Whole-Shoe Disinfection Device at Three Time Points, NSF International—Applied Research Center, 789 N. Dixboro Rd. Ann Arbor, MI 48015, USA, Aug. 27, 2019.

\* cited by examiner

INSTANT-ON HANDHELD SANITIZER

BACKGROUND OF THE INVENTION

It is known that the rising problem of antibiotic resistance has led to fears that medicine will return to the situation of a century ago when extensive wounds and surgery often led to death due to uncontrollable infection. These fears have in turn spurred a major research effort to find alternative antimicrobial approaches which, it is hypothesized, will kill ultra-resistant micro-organisms while being unlikely to cause additional resistance to develop. At the present time many international research efforts to discovery new antimicrobials are underway. Recently, the emphasis is on how to take precautions against creating, and if possible eliminate multidrug resistance in concert with exploring new methods to kill pathogenic microorganisms. Karen et al. in "Tackling antibiotic resistance," Bush K, *Nat Rev Microbiol.* 2011 Nov. 2; 9(12):894-6, pointed out that the investigation of novel non-antibiotic approaches, which can prevent and protect against infectious diseases should be encouraged, and should be looked upon as a high-priority for research and development projects.

One source of sterilization is UV-C radiation (wavelength: 200-280 nm). Among this wavelength range, the optimum range of 250-270 nm has the best potential ability to inactivate microorganisms because it this wavelength is absorbed by nucleic acids of microbial cells and, therefore is the most lethal range of wavelengths.

One way to reduce infection by resistant (or non-resistant) microorganisms is to neutralize as many of such organisms from the environment as possible. As some such organisms spread through the air, HEPA filters are often used to filter out such organisms before they infect humans, but many such organisms are transmitted on surfaces such as hands and shoes of people entering the area. To this, often before entering these areas, staff/patients must kill organisms from their hands using a germicidal compound or washing their hands. This helps keep microorganisms from spreading by way of hands, but what about the microorganisms that are on surfaces such as tables, clothing, instruments, and wounds?

Applying chemical products to such areas is partially effective. To kill or disable most pathogens, a very strong chemical is required. As the strength of the chemical increases, so does the risk of potential hazards to health and safety of both the people applying the chemical and to the users of the cleaned surfaces. This is not to mention issues related to allergies. Stronger chemicals tend to impact/discolor the surfaces on which they are applied, and many are not usable on a person. For example, bleach (chorine) is a known effective disinfectant, but bleach applied to clothing will result in decolorization and eventual decomposition. Furthermore, bleach (chlorine) does not kill many pathogens that have a protective shell (e.g., MRSA).

Beyond hospitals, many other areas are also prone to breed germs/microbes. For example, public showers in gyms, schools, etc.

UV radiation emitting devices (ultraviolet emitters or ultraviolet light bulbs) emit light with wavelengths of between, for example, 400-100 nm. Such ultraviolet light is known to kill at least a subset of known pathogens and, therefore, this light is suitable to reduce the number of pathogens on a surface.

Although ultraviolet light kills some pathogens and is suitable for that purpose, ultraviolet radiation alone is not effective in killing certain pathogens or classes of pathogens, especially pathogens that have protective envelopes or shells that protect the pathogens from the environment until the pathogens find their way into a suitable environment for growth, such as a wound. An example of such a pathogen is C-diff, which has a hard outer shell and is not significantly affected by UVC radiation. Bleach has been found effective in breaking this outer shell and killing C-diff, but bleach is impractical for use on many surfaces.

Lower wavelengths of ultraviolet light will ionize oxygen producing ozone ($O_3$). For many uses of ultraviolet light, ozone ($O_3$) production is an unwanted side effect of ultraviolet lamps. For such uses, many ultraviolet lamps are treated/coated with a material that absorbs ultraviolet light wavelengths below 254 nm since these lower wavelengths of ultraviolet light will ionize oxygen and for many applications, the production of ozone is unwanted.

Ozone has been found to be effective in killing some pathogens that cannot be effectively killed with ultraviolet light alone. Ozone is a strong oxidizing agent that breaks through the encapsulation of some of the more difficult pathogens to kill such as C-diff. Ozone is effective in bacterial disinfection and the inactivation of many viruses. Therefore, it is preferred to use radiation emitting devices that emit ultraviolet light in approximately the 240-250 nm range (e.g., emitters without the above noted coating) while also emitting shorter wavelength ultraviolet light (e.g., approximately 180 nm) for the production of ozone in the presence of oxygen ($O_2$).

Such specialized radiation emitting devices that do not have the surface treatment that filter out the 180 nm wavelengths are known and in use in other applications such as water sanitation, often known as germicidal lamps. These radiation emitting devices are usually mercury vapor tubes like typical fluorescent light bulbs but without any phosphor coating and without any material that impedes the passing of ultraviolet light, including ultraviolet light in the 253.7 wavelength range which is very good at destroying pathogens. These radiation emitting devices emit a broader range of ultraviolet that includes the 254 nm wavelength and also shorter wavelengths (e.g., less than 240 nm) that break the bond between dioxygen molecules ($O_2+UV \rightarrow 2O$), then the unstable oxygen atoms bond with another dioxygen molecule ($O_2+O \rightarrow O_3$) forming ozone.

Unfortunately, these radiation emitting devices are costly and have limited bulb life. As the intended use in a handheld sanitizing device, these bulbs are often mounted in an enclosure that is small enough to be handheld and it is difficult to replace the bulbs (radiation emitting devices) in the field due to special precautions in handling and disposal of the radiation emitting devices (bulbs). Further, it is often difficult to determine when a failure occurs as the bulbs/emitters emit very little visible light.

In handheld operation, the user typically aims the handheld device at an area that is to be sanitized (e.g., a table, clothing, instrument, wound) then initiates exposure to UV light by pressing a button/trigger. As many radiation emitting devices are mercury vapor gas discharge bulbs, there is often a considerable delay between energizing these radiation emitting devices and when sufficient UV radiation is emitted. For a handheld device, this delay is not desirable as the user (the person pressing the trigger) may not expose the area that is to be sanitized for sufficient time to achieve sufficient UV exposure for creating ozone and killing microbes.

These bulbs/emitters often have an expected life based upon the manufacturer's testing. One reason for these bulbs/emitters premature failure is from power on/off cycles, just like many other types of emitters (e.g., fluorescent light bulbs). More stress is exerted on a bulb/emitter when it is powered on than when the bulb/emitter remains operation. For example, most incandescent or fluorescent bulbs fail when they are turned on as the heater/filament heat and expand/contract. In the example of mercury vapor lamps, premature failure is often due to fast temperature changes that occur when the mercury is vaporized. Although emissions of small amounts of ultraviolet light are minimal risks to health, it is not desirable to constantly emit significant amounts of ultraviolet light from a floor-mounted device as there are health risks from such emissions. Therefore, it is not desirable to constantly emit ultraviolet radiation from these floor-mounted foot sanitization devices. In the past, a sensor was deployed to signal when a foot/shoe was placed atop these floor-mounted devices and, power was provided to the ultraviolet bulbs in response to that signal. Unfortunately, this causes many on/off cycles, decreasing the life of the ultraviolet bulbs.

What is needed is a handheld sanitization system that will provide fast-response UV light while extending the life of the radiation emitting devices.

SUMMARY OF THE INVENTION

Mechanisms are disclosed to emit the ultraviolet light (and generate ozone) when a trigger is operated, without fully powering on, then powering off the ultraviolet bulbs. The mechanisms include one or more of louvers or shutters and/or reducing power to the ultraviolet bulbs, but not disconnecting power to the ultraviolet bulbs and, therefore, maintaining the highest possible ultraviolet bulb life. In some embodiments, the shutter/louver mechanism is completely mechanical such that the louvers/shutters open upon force applied to a trigger and close when the force applied to the trigger abates. In some embodiments, the shutter/louver mechanism is electromechanically controlled such that the louvers/shutters are opened by an electromechanical device (e.g., any electromechanical device the imparts movement such as a solenoid, motor, servo motor, micromachine, etc.) upon closing of a trigger switch and are closed when the trigger switch opens. In some embodiments, a sensor detects where the handheld sanitizer is aimed and disables the shutter/louver mechanism from operation unless the handheld device is aimed downwardly.

In one embodiment, a handheld sanitization device for sanitizing a surface using ultraviolet light and ozone is disclosed including at least one ultraviolet emitter housed within an enclosure. The enclosure has a window for passing the ultraviolet light from the at least one ultraviolet emitter and onto the surface and the at least one ultraviolet emitter is continuously powered to emit the ultraviolet light (e.g., when power is available). There is a mechanism for selectively blocking the window that has an open position in which the ultraviolet light passes through the window and out of the enclosure and has a closed position in which the window is occluded, thereby blocking the passage of the ultraviolet light from the at least one ultraviolet emitter, through the window and out of the enclosure. The mechanism for selectively blocking the window is biased into the closed position. There is an electromechanical device physically interfaced between the enclosure and the mechanism for selectively blocking the window and there is a trigger switch electrically coupled to the electromechanical device. Responsive to operation of the trigger switch, the mechanism for selectively blocking the window is moved from the closed position into the open position by movement of the electromechanical device, thereby, releasing the ultraviolet light through the window.

In another embodiment, a handheld sanitization device for sanitizing a surface using ultraviolet light and ozone is disclosed including at least one ultraviolet emitter housed within an enclosure. The enclosure has a window for passing the ultraviolet light from the at least one ultraviolet emitter and onto the surface and the at least one ultraviolet emitter is continuously powered to emit the ultraviolet light. A louver is positioned behind the window and has a fixed blocking section interfaced to the enclosure and has a movable blocking section slideably interfaced to the enclosure, the movable blocking section is movable between an open position in which the movable blocking section aligns with the fixed blocking section, thereby allowing the ultraviolet light to pass from the at least one ultraviolet emitter through the window and out of the enclosure and has a closed position in which fixed blocking section and the movable blocking section prevent the ultraviolet light from exiting the enclosure through the window. The movable blocking section is biased into the closed position. There is an electromechanical device interfaced between the enclosure and the movable blocking section and a trigger switch electrically coupled to the electromechanical device. Responsive to operation of the trigger switch, the movable blocking section is moved from the closed position into the open position by movement of the electromechanical device, thereby, releasing the ultraviolet light through the window.

In another embodiment, a method of sanitizing a surface using ultraviolet light and ozone is disclosed including at least one ultraviolet emitter housed within an enclosure. The enclosure has a window for passing the ultraviolet light from the at least one ultraviolet emitter and onto the surface and the at least one ultraviolet emitter continuously powered to emit the ultraviolet light. There is at least one shutter positioned behind the window rotatably interfaced to the enclosure. The at least one shutter rotates between an open position in which each of the at least one shutter are at an angle of between 75 and 115 degrees with respect to the window, thereby allowing the ultraviolet light to pass from the at least one ultraviolet emitter through the window and out of the enclosure and the at least one shutter has a closed position in which each of the at least one shutter is parallel with or at an angle of less than 10 degrees with respect to the window, thereby preventing the ultraviolet light from exiting the enclosure through the window. The at least one shutter is biased into the closed position. There is an electromechanical device interfaced between the enclosure and each of the at least one shutter and a trigger switch electrically coupled to the electromechanical device. Responsive to operation of the trigger switch, each of the at least one shutter is rotated from the closed position into the open position by movement of the electromechanical device, thereby, the ultraviolet light passes through the window.

BRIEF DESCRIPTION OF DRAWINGS

The invention can be best understood by those having ordinary skill in the art by reference to the following detailed description when considered in conjunction with the accompanying drawings in which.

DETAILED DESCRIPTION OF THE INVENTION

Figure 1:
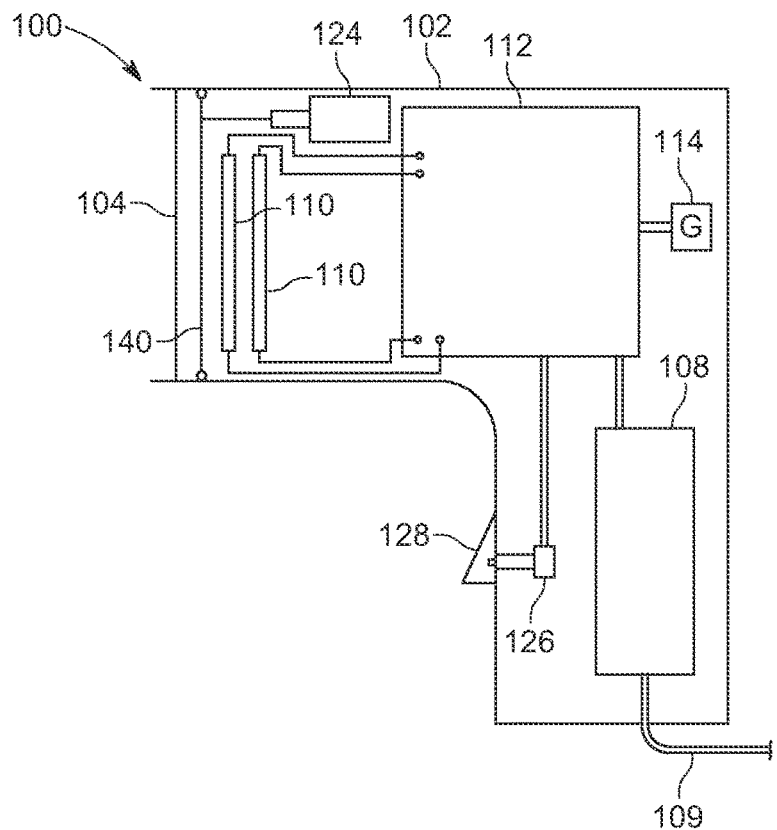
FIG. 1 illustrates a side-cutaway view of a handheld sanitization device with louvers/shutters being powered by an external source.

Reference will now be made in detail to the presently preferred embodiments of the invention, examples of which are illustrated in the accompanying drawings. Throughout the following detailed description, the same reference numerals refer to the same elements in all figures.

Throughout the remainder of this description, the term "pathogen" will be used generically to denote any germ, virus, prion, fungus, spore, microbe, or other pathogen, capable or not capable of infecting a mammal such as a human.

The term louvers/shutters represent any such device or similar device that has at least two modes (e.g., positions), one in which light passes through the louvers/shutters and one in which light is blocked by the louvers/shutters.

Additionally, the described system is shown in detail for exposing a surface to ultraviolet light and ozone ($O_3$). There are many surfaces that are ideal for sanitizing using ultraviolet light and ozone including, but not limited to, tables, instruments, clothing, hands, wounds, floors and tools. Note that there are known risks of exposing certain parts of a mammal's body to certain wavelengths of ultraviolet light, therefore, it is anticipated that proper precautions are taken to reduce exposure to such and, therefore, reduce such risks.

For brevity, various mechanical and electrical subcomponents such as supports, screws, wires, etc., are not described as such are well known in the art.

Figure 2:
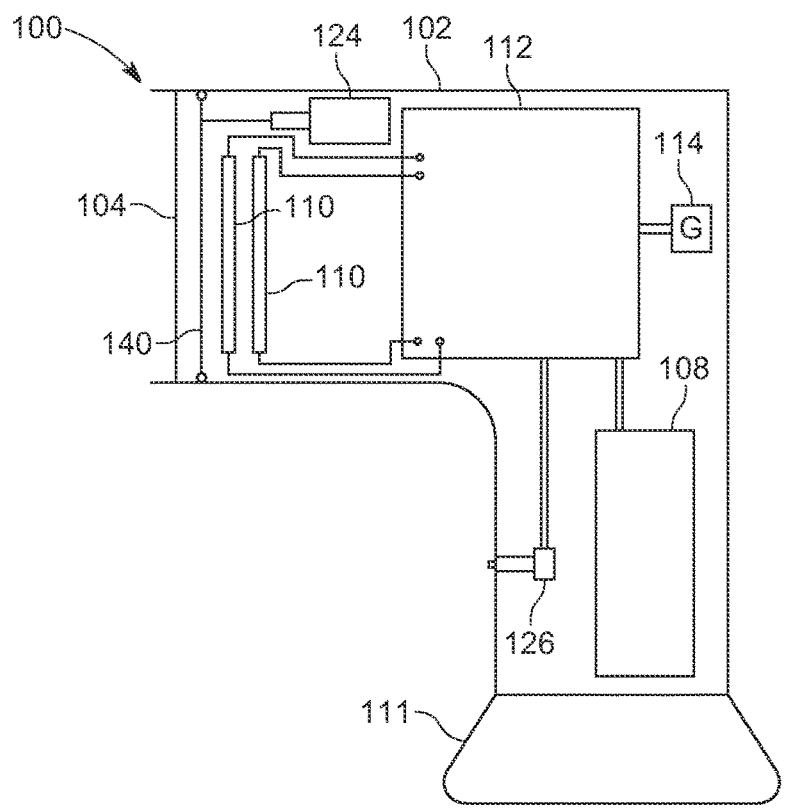
FIG. 2 illustrates a side-cutaway view of the handheld sanitization device with louvers/shutters being battery powered.

Referring to FIGS. 1 and, 2, cross-sectional views of a handheld sanitization device with louvers/shutters 100 are shown. The handheld sanitization device with louvers/shutters 100 in FIG. 1 is powered by external power 109 such as typical AC line voltage (e.g., 117 VAC). The handheld sanitization device with louvers/shutters 100 in FIG. 2 is powered by a battery pack 111 such as a typical rechargeable battery pack as used with cordless drills.

The handheld sanitization device with louvers/shutters 100 has ultraviolet emitters 110 that continuously emit ultraviolet light at some intensity as long as power is provided. The ultraviolet emitters 110 are typically mercury vapor tubes without any coating material that impedes the passing of ultraviolet light, including ultraviolet light which is good at destroying pathogens. The ultraviolet emitters 110 emit a broad range of ultraviolet that includes the 254 nm wavelength (e.g., 253.7 nm) and also emit shorter wavelength ultraviolet light (e.g., approximately 180 nm) for the production of ozone in the presence of oxygen ($O_2$). The shorter wavelength ultraviolet light will break the bond between dioxygen molecules ($O_2+UV \rightarrow 2O$), then the unstable oxygen atoms bond with another dioxygen molecule ($O_2+O \rightarrow O_3$) forming ozone. The ozone will help in destroying pathogens that are not easily destroyed solely with the ultraviolet light.

As the ultraviolet emitters 110 are typically mercury vapor tubes or the like, frequent power cycles often lead to reduced life of the ultraviolet emitters 110 and, upon failure, the handheld sanitization device with louvers/shutters 100 must be serviced as handling of such ultraviolet emitters 110 requires care for safety and proper disposal. Such servicing is expensive as the ultraviolet emitters 110 are costly. Furthermore, in use, any delay between operation of the trigger 128 and emission of ultraviolet light (and production of ozone) reduces the efficacy of the handheld sanitization device with louvers/shutters 100. Therefore, it is desired that upon operation of the trigger 128, emission of the ultraviolet light commences instantaneously (e.g., within a few milliseconds).

To increase the life of the ultraviolet emitters 110 and increase the speed of irradiation by the ultraviolet light, the handheld sanitization device with louvers/shutters 100 maintains constant operation of the ultraviolet emitters 110 (either full power or reduced power) and selectively blanks, occludes, or covers the ultraviolet emitters 110 until a user presses or operates the trigger 128. Upon operation of the trigger 128, the louvers/shutters are opened, thereby allowing ultraviolet light to escape and radiate the targeted surface with ultraviolet light and to create ozone from oxygen molecules between the handheld sanitization device with louvers/shutters 100 and the surface. To impact this operation, the handheld sanitization device with louvers/shutters 100 has an enclosure 102 that is sealed so that any ozone created within the enclosure 102 remains within the enclosure 102. An end of the enclosure 102 is covered or sealed with a window 104 made from a material that allows passage of all desired wavelengths of ultraviolet light, for example, fused silica or fused quartz. As the ultraviolet emitters 110 emit the approximately 254 nm wavelength (e.g., 253.7 nm) and the approximately 180 nm wavelength, ozone is produced in the presence of oxygen ($O_2$) within the enclosure.

As the enclosure is sealed, the enclosure will not allow the escape of this ozone and ozone emission is limited to that created between the window 104 and the surface at which the handheld sanitization device with louvers/shutters 100 is aimed for destroying pathogens. Note that although the enclosure 102 is shaped in a gun-like form, there is no restriction as to the overall shape or size of the enclosure 102.

In the embodiments disclosed, the shutter/louver 140 is shown coupled to an electromechanical control device 124 (e.g., any electromechanical device the imparts movement such as a solenoid, motor, servo motor, micromachine, etc.), though it is equally anticipated that the shutter/louver 140 is coupled to the trigger 128 by mechanical linkages, which are not shown for brevity and clarity reasons.

Electrical power from the circuit board 112 controls the electromechanical control device 124 to open/close the shutter/louver 140 and, allow the escape of ultraviolet light (open position) or block the escape of ultraviolet light (closed position). Note that although an electromechanical control device 124 is shown, as above, it is also fully anticipated that the shutter/louver be mechanically coupled to the trigger 128 and mechanical operation of the trigger 128 opens/closes the shutter/louver 140, but it should be noted that a mechanical-only operation prevents certain features such as detecting where the handheld sanitization device with louvers/shutters 100 is aimed and control of the power provided to the ultraviolet emitters 110.

In the schematics of FIGS. 1 and 2, the trigger 128 (e.g., a mechanical trigger) is coupled to a trigger switch 126. The trigger switch 126 signals the circuit board 112 and, dependent upon whether the trigger switch 126 is open or closed, the circuit board 112 controls power to the ultraviolet emitters 110 and to the electromechanical control device 124 to control the shutter/louver 140 to move between the open position and the closed position, thereby controlling emission of ultraviolet light through the window 104.

For completeness, a power supply 108 is shown for converting external power 109 or power from the battery pack 111 into the voltages required by the circuit board 112 and the ultraviolet emitters 110.

To increase the life of the ultraviolet emitters 110 and provide fast response to operation of the trigger 128, the handheld sanitization device with louvers/shutters 100 maintains constant operation of the ultraviolet emitters 110. In some embodiments, the ultraviolet emitters 110 are constantly operated at full power while in other embodiments, the ultraviolet emitters are operated at reduced power when the shutter/louver 140 is in the closed position (e.g., when the trigger 128 is not operated) and at full power when the shutter/louver 140 is in the open position (e.g., when the trigger 128 is operated). As it is not desired that ultraviolet light constantly escape through the window 104, the handheld sanitization device with louvers/shutters 100 selectively blanks, occludes, or blocks passage of light from the ultraviolet emitters 110 to the window 104. It should be noted that such blocking will block a large percentage of the ultraviolet light (e.g., 98-100%), but it is anticipated that a small amount of ultraviolet light will occur. The net effect is to reduce the emission of ultraviolet light from the window 104 until a user operates the trigger 128.

To impact this operation, the handheld sanitization device with louvers/shutters 100 has one or more ultraviolet emitters 110 that constantly emit ultraviolet light when the handheld sanitization device with louvers/shutters 100 is in an operating mode (e.g., powered, turned on, the battery back 111 connected). As the ultraviolet emitters emit the approximately 254 nm wavelength (e.g., 253.7 nm) and the approximately 180 nm wavelength, ozone is produced in the presence of oxygen ($O_2$) within the enclosure. As the enclosure is sealed, the enclosure will not allow the escape of this ozone and ozone emission is limited to that created between the window 104 and the targeted surface for destroying pathogens.

Figure 3:
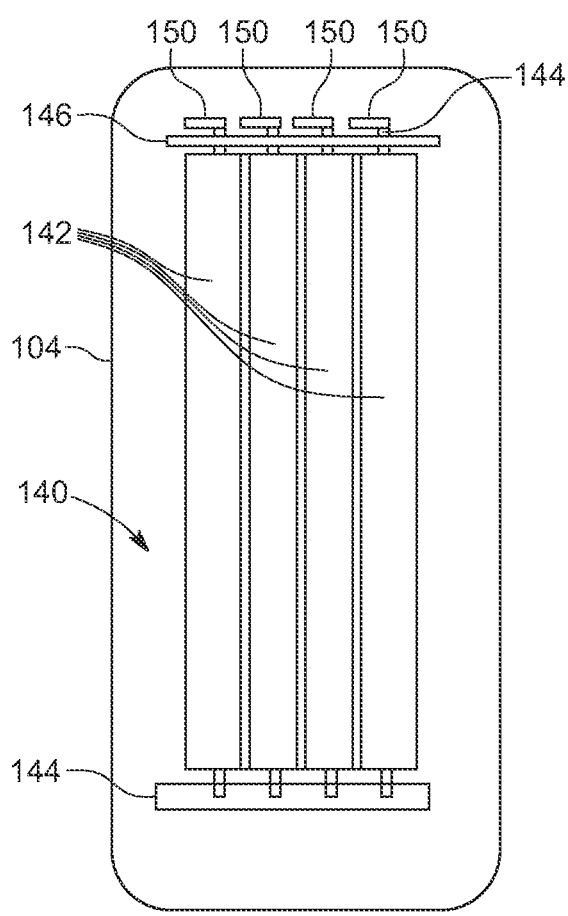
FIG. 3 illustrates a plan view of the handheld sanitization device with louvers/shutters showing shutters in a closed position.

Referring to FIGS. 3, 4, 5, and 6, views of the handheld sanitization device with louvers/shutters 100 are shown with the shutter/louvers 140 being shutters 142. In FIG. 3, the shutters 142 are shown in the closed position and the shutter control arms 150 are shown somewhat parallel to the shutters 142. It should be noted that there are may mechanisms possible to open/close shutters and what is shown is an example of one such mechanism. The shutters 142 are shown looking in through the window 104 and, in some embodiments, have a bezel (not shown for clarity and brevity reasons). The shutters 142 (when in the closed position) and bezel are situated between the ultraviolet emitters 110 and the window 104 to block ultraviolet light from escaping the enclosure 102 through the window 104 when the shutters 142 are in the closed position as in FIG. 3. In this example, the shutters are rotatably held by brackets 144/146.

Figure 4:
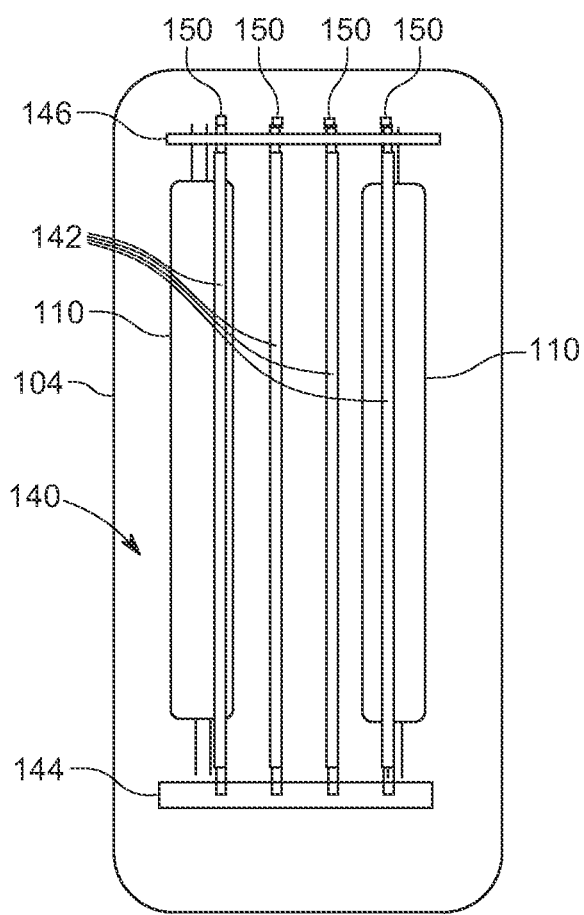
FIG. 4 illustrates a plan view of the handheld sanitization device with louvers/shutters showing shutters in an open position.

In FIG. 4, the shutters 142 are shown in the open position. As will be shown in FIGS. 5 and 6, the shutter control arms 150 are pulled/pushed by the electromechanical control device 124 (e.g., a solenoid or motor), thereby rotating the shutters 142 between the closed position as in FIG. 3 and the open position as in FIG. 4. In the open position, the ultraviolet emitters 110 are now visible through the window 104 and, therefore, if the ultraviolet emitters 110 are powered and emitting ultraviolet light, the ultraviolet light will pass through the window 104 and irradiate the surface at which the handheld sanitization device with louvers/shutters 100 is aimed.

Figure 5:
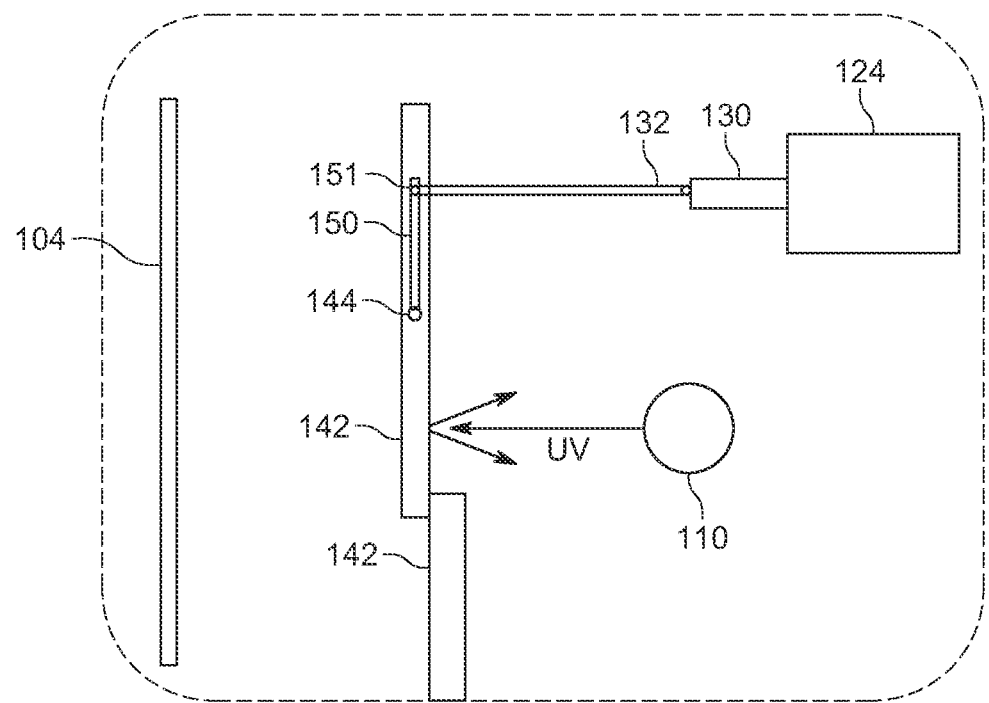
FIG. 5 illustrates a schematic view of the handheld sanitization device with louvers/shutters showing operation of the shutters in the closed position.
Figure 6:
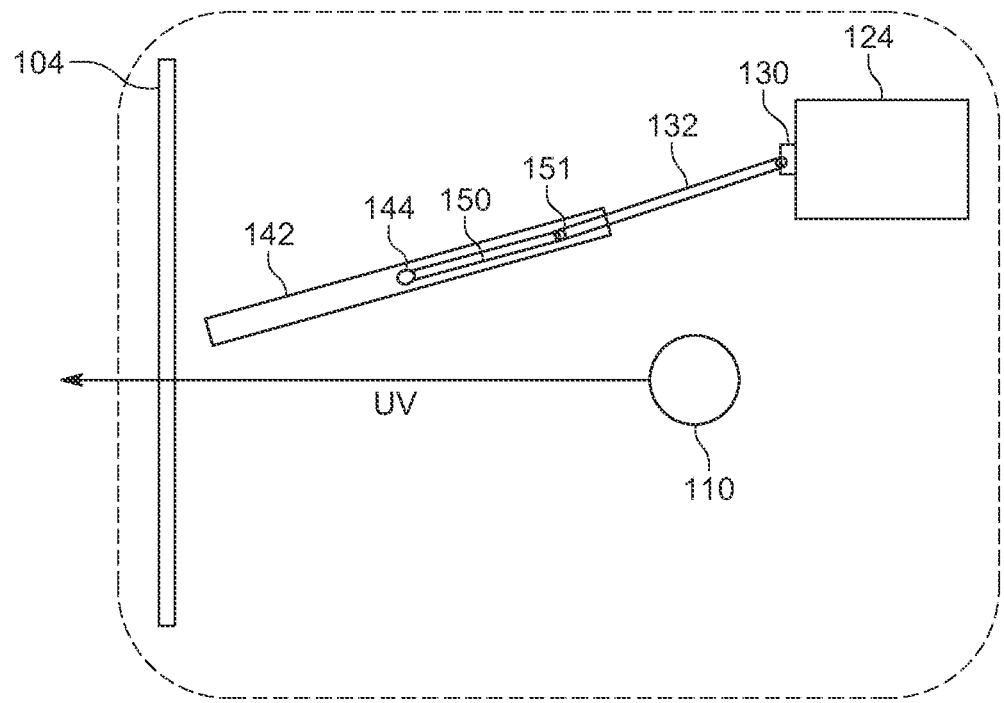
FIG. 6 illustrates a schematic view of the handheld sanitization device with louvers/shutters showing operation of the shutters in the open position.

FIGS. 5 and 6 show a detailed example of the operation of the shutters 142. In FIG. 5, the electromechanical control device 124 (shown as a solenoid) has a core 130 that is extended (note that many electromechanical control devices 124 have internal springs to extend the core 130 until power is applied to the windings of the electromechanical control device 124). The core 130 is interfaced to the shutters 142 by a shutter arm 132 that connects to the shutter control arm(s) 150 at a shutter control arm interface point 151. Only a pivot point of the bracket 144 is shown so as not to occlude the shutter 142. Therefore, when the electromechanical control device 124 is not powered, each of the shutters 142 is substantially parallel to the window 104 and overlap (e.g., each of the shutters 142 touch each other at an end). As such, the shutters 142 are in the closed position and ultraviolet light from the emitters 110 is blocked by the shutters 142 and not allowed to exit the enclosure 102 through the window 104. Note that the shutter 142 being substantially parallel to the window 104 allows for multiple shutters 142 and each of the shutters are allowed to be at a slight angle, for example, less than 10 degrees with respect to the window 104. The angle is not important, only the blocking of ultraviolet light from escaping through the window 104 is needed. Note that in some embodiments, a small amount of leakage is acceptable.

In FIG. 6, power is applied to the windings of the electromechanical control device 124 (shown as a solenoid) and the core 130 that is retracted 124. The core 130 pulls the shutter arm 132 which pulls the shutter control arm(s) 150. Therefore, when the electromechanical control device 124 is powered, each of the shutters 142 is substantially perpendicular to the window 104. As such, the shutters 142 are in the open position and ultraviolet light from the emitters 110 is allowed to exit the enclosure 102 through the window 104. Note that the shutter 142 being substantially perpendicular to the window 104 allows each of the shutters to be at a slight angle such as at an angle of between 75 and 115 degrees with respect to the window. This angle is not critical, as long as sufficient ultraviolet light escapes through the window 104.

Figure 7:
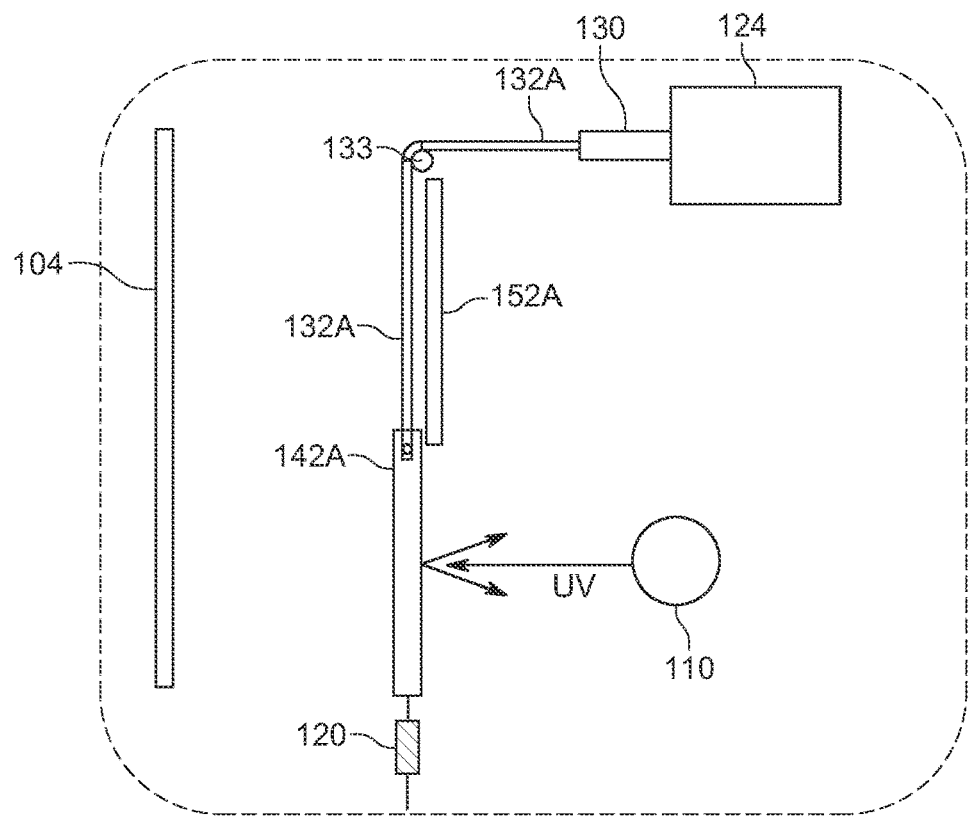
FIG. 7 illustrates a schematic view of the handheld sanitization device with louvers/shutters showing louvers in a closed position.
Figure 8:
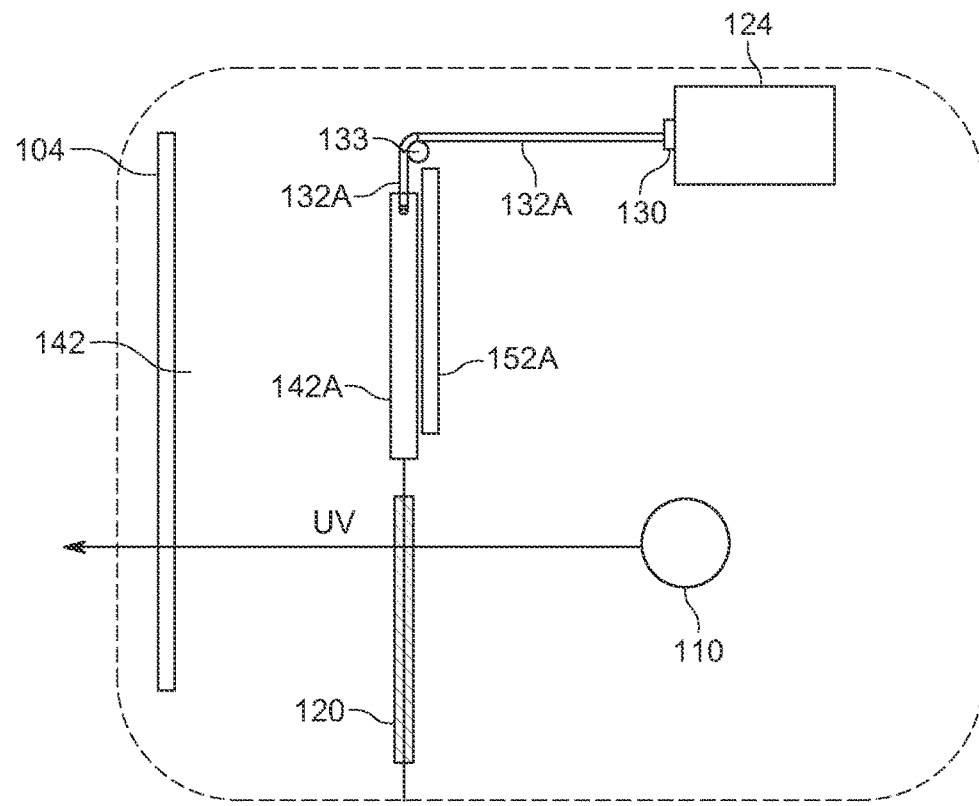
FIG. 8 illustrates a schematic view of the handheld sanitization device with louvers/shutters showing louvers in an open position.

Referring to FIGS. 7 and 8, schematic views of the handheld sanitization device with louvers/shutters 100 are shown with the louvers/shutters 140 being louvers 142A/152A. In FIG. 7, the electromechanical control device 124 (shown as a solenoid) has a core 130 that is extended (note that many electromechanical control devices 124 have internal springs to extend the core 130 until power is applied to the windings of the electromechanical control device 124). The core 130 is interfaced to a movable louver 142A by a cable 132A that changes direction in this example by way of a pully 133. In this example, the movable louver 142A is biased in the closed position by a spring 120. A fixed louver 152A in combination with the movable louver 142A being in the closed position blocks ultraviolet light from the ultraviolet emitters 110 from exiting through the window 104. Therefore, when the electromechanical control device 124 is not powered, ultraviolet light from the emitters 110 is blocked by the louver 142A/152A and not allowed to exit the enclosure 102 through the window 104.

In FIG. 8, power is applied to the windings of the electromechanical control device 124 (shown as a solenoid) and the core 130 that is retracted 124. The core 130 pulls the cable 132A which pulls the movable louver 142A to the open position. Therefore, when the electromechanical control device 124 is powered the movable louver 142A and the fixed louver 152A overlap, leaving an opening for the ultraviolet light to pass from the ultraviolet emitters 110 and out of the enclosure through the window 104.

Figure 9:
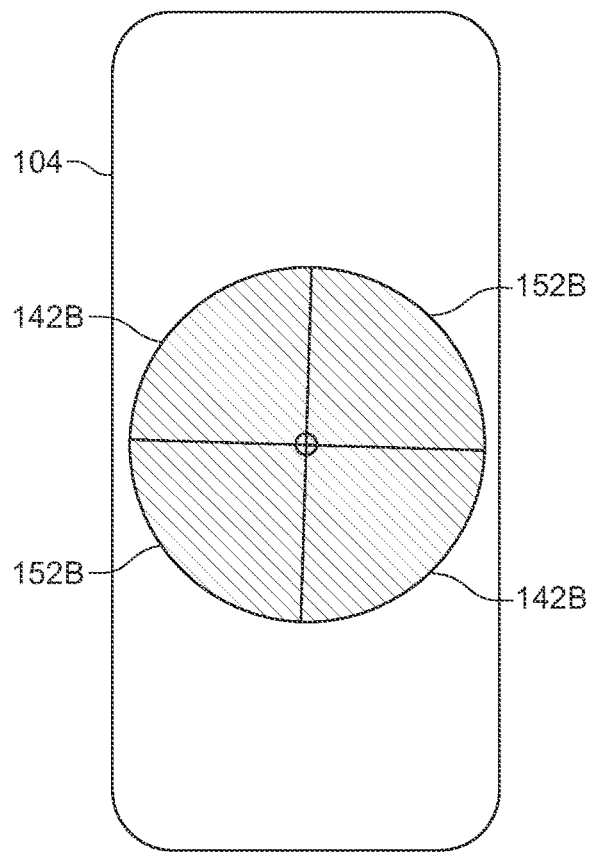
FIG. 9 illustrates a schematic view of the handheld sanitization device with louvers/shutters showing operation of a rotating shutter in the closed position.
Figure 10:
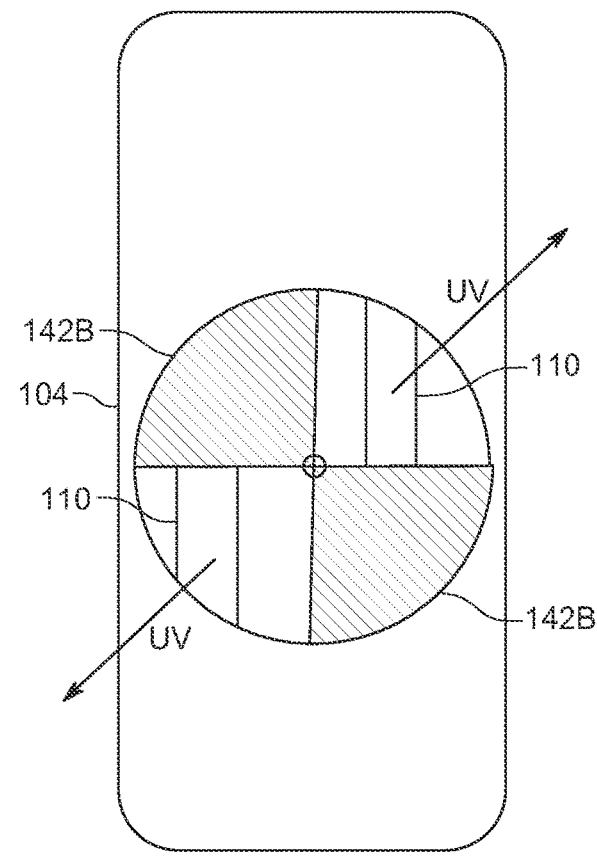
FIG. 10 illustrates a schematic view of the handheld sanitization device with louvers/shutters showing operation of a rotating shutter in the open position.

Referring to FIGS. 9 and 10, schematic view of the handheld sanitization device with louvers/shutters 100 are shown with the louvers/shutters 140 being rotating louvers 142B/152B or an iris. In FIG. 9, the closed position is shown in which the movable rotating louver 142B and the stationary louver 152B do not overlap substantially and, therefore, little, or no ultraviolet light from the ultraviolet emitters escapes through the window 104. In FIG. 10, the open position is shown in which the movable rotating louver 142B has been rotated by electromechanical control device 124 (e.g., a motor, servo, solenoid) and the rotating louver 142B and the stationary louver 152B now overlap substantially and, therefore, the ultraviolet emitters 110 are visible through the window 104 and, therefore, ultraviolet light from the ultraviolet emitters escapes through the window 104.

Figure 11:
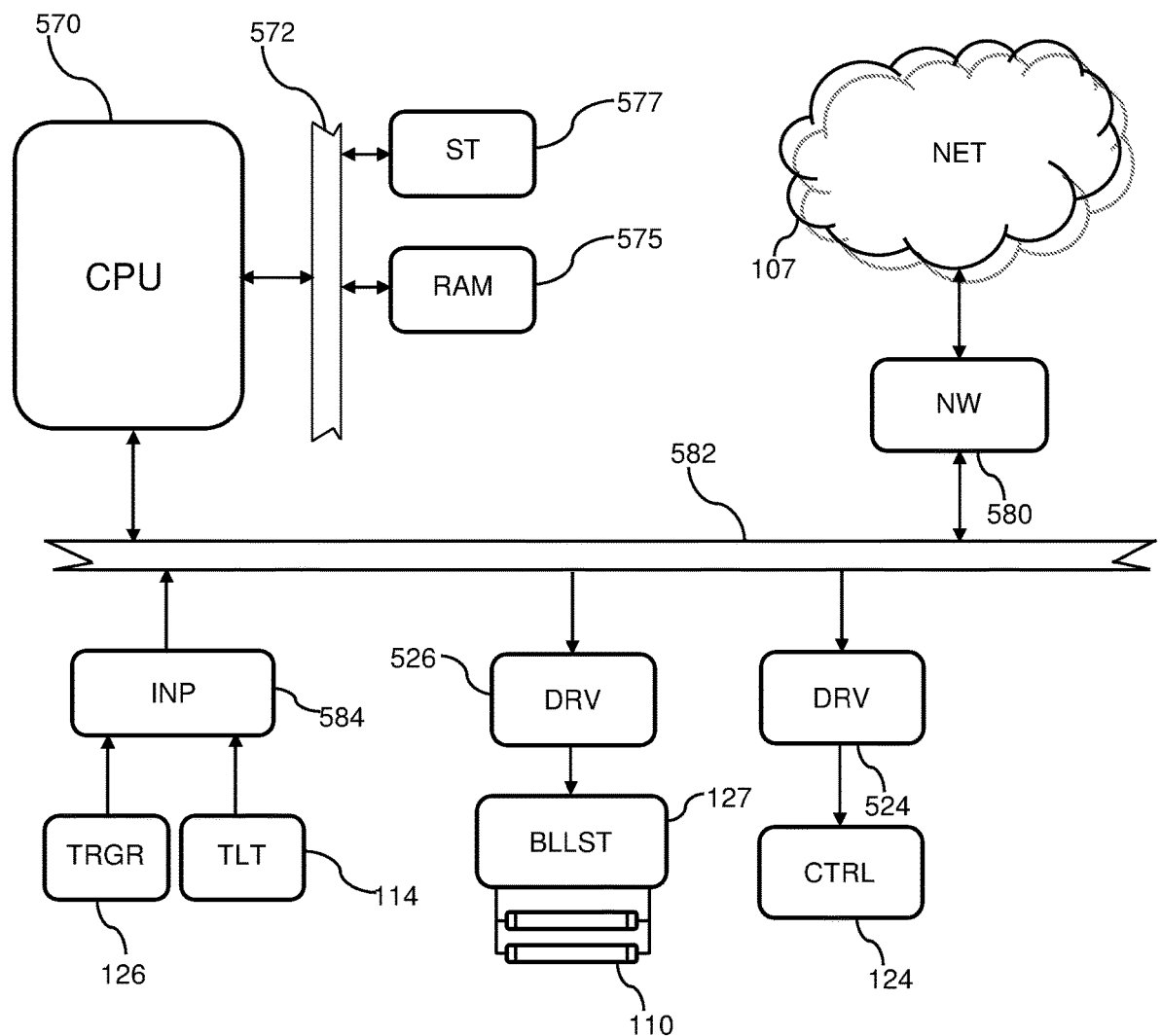
FIG. 11 illustrates a schematic diagram of the handheld sanitization device.

Referring to FIG. 11, a schematic diagram of the handheld sanitization device with louvers/shutters 100 is shown. In this embodiment, the circuit board 112 includes a processor or microcontroller, referred to as a CPU 570. Interfaced to the CPU 570 is data storage 577 for storing programs, etc., and random-access memory 575. In some embodiments, the data storage and random-access memory 575 are interfaced to the CPU by a memory bus 572 or any way known in the industry (e.g., internal storage). In some embodiments, there is a system bus 582 for connecting to input/output subsystems, though it is fully anticipated that the CPU 570 is a microcontroller having internal input/output circuitry. In such embodiments, the trigger switch 126 and optional tilt sensor 114 are interfaced to an input port 584 that is either internal to the CPU 570 or interfaced by way of an input port 584 interfaced to the system bus 582. The ballast(s) 127 that drive the ultraviolet emitters 110 are controlled by a driver 526 that is either internal to the CPU 570 or interfaced to the system bus 582. Likewise, the electromechanical control device 124 is interfaced to a second driver 524 that is either internal to the CPU 570 or interfaced to the system bus 582.

In some embodiments, a wireless interface 580 is provided for communication wirelessly through a network 107 to report on activity and to signal any failures, such as failure of one of the ultraviolet emitters 110. When the wireless interface 580 is provided, it is also anticipated that, in some embodiments, each the handheld sanitization device with louvers/shutters 100 is enabled/disabled through the network 107.

Figure 12:
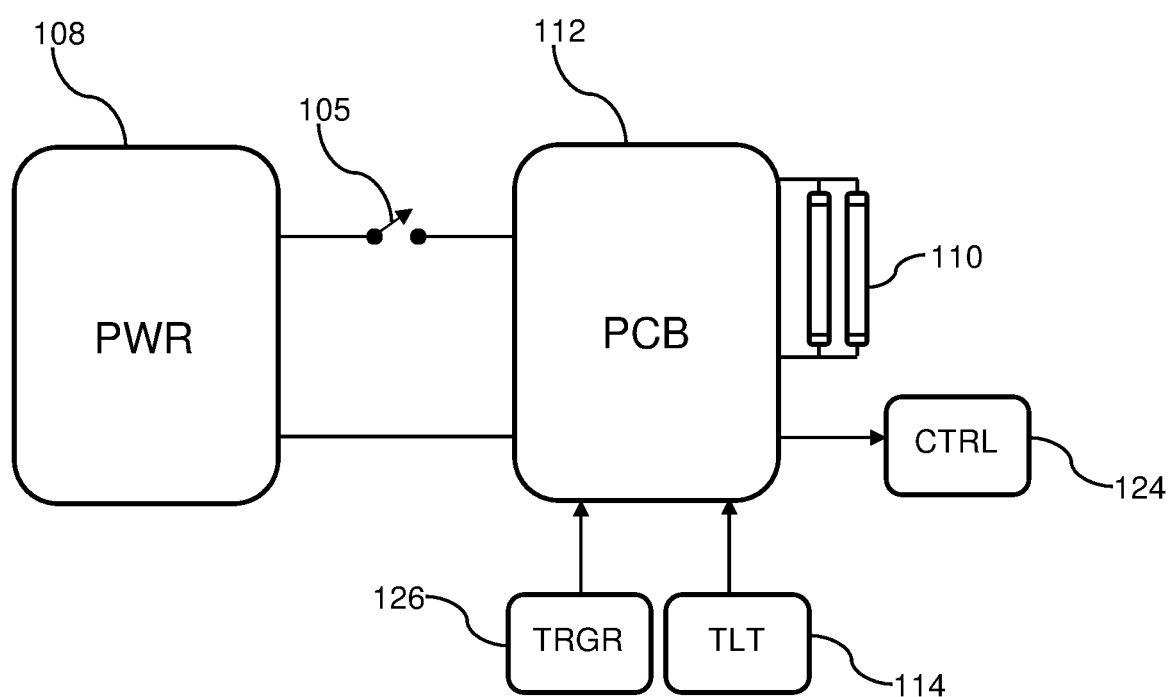
FIG. 12 illustrates a block diagram of the handheld sanitization device.

Referring to FIG. 12, a block diagram of the handheld sanitization device with louvers/shutters 100 is shown. The circuit board 112 receives power from the power supply 108. In this embodiment, there is a power on/off switch 105 that turns off power to the handheld sanitization device with louvers/shutters 100, for example, when the handheld sanitization device with louvers/shutters 100 is not to be used for extended periods of time. In this example, the ballasts 127 are integrated or mounted on the circuit board 112 and provide the requisite power to the ultraviolet emitters 110. The circuit board 112 is connected to energize/de-energize the electromechanical control device 124 and inputs from the trigger switch 126 and the optional tilt sensor 114 are connected to the circuit board 112. In some embodiments, the functions of the handheld sanitization device with louvers/shutters 100 are implemented using a processor/CPU 570 as above, while in some embodiments, the circuit board 112 includes discrete logic that implements the functions of the handheld sanitization device with louvers/shutters 100.

Figure 13:
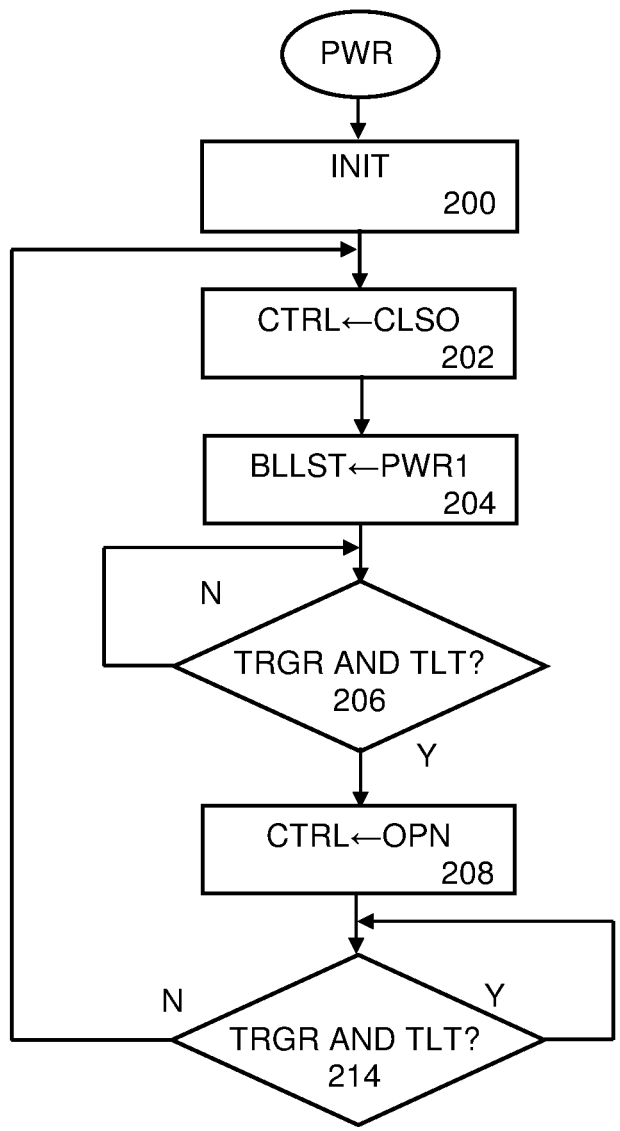
FIG. 13 illustrates a flow diagram of the handheld sanitization device having the optional tilt sensor and providing constant power to the ultraviolet emitters.

Referring to FIGS. 13, 14, 15, and 16, flow diagrams of the handheld sanitization device with louvers/shutters 100 are shown. FIG. 13 shows a typical program flow of the handheld sanitization device with louvers/shutters 100 with the optional tilt sensor and providing constant power to the ultraviolet emitters. After initialization 200, the electromechanical control device 124 is controlled 202 to close the shutter/louver 140 and the ballast 127 is controlled 204 to power the ultraviolet emitters 110 with a first power level (e.g., 100% power). Now when it is detected 206 that the trigger switch is off or the optional tilt sensor 114 indicates improper 202 orientation of the handheld sanitization device with louvers/shutters 100, the electromechanical control device 124 is controlled 202 to close the shutter/louver 140 and the above continues.

Figure 14:
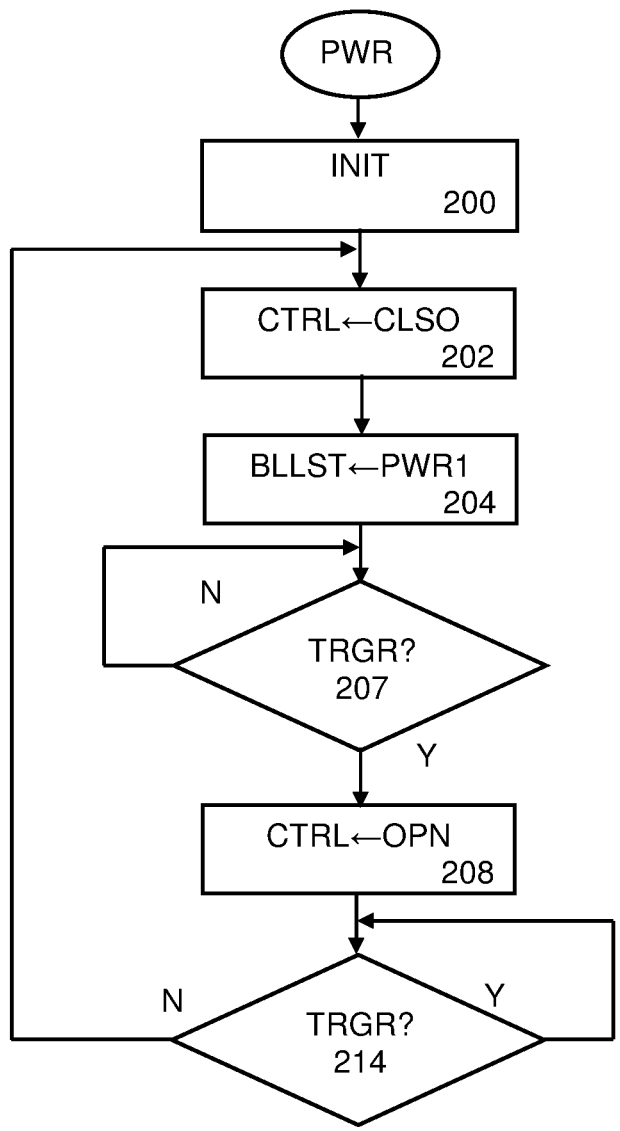
FIG. 14 illustrates a flow diagram of the handheld sanitization device without the optional tilt sensor and providing constant power to the ultraviolet emitters.

FIG. 14 shows a typical program flow of the handheld sanitization device with louvers/shutters 100 without the optional tilt sensor and providing constant power to the ultraviolet emitters. After initialization 200, the electromechanical control device 124 is controlled 202 to close the shutter/louver 140 and the ballast 127 is controlled to power the ultraviolet emitters 110 with a first power level (e.g., 100%). When it is detected 207 that the trigger switch is on, the electromechanical control device 124 is controlled to open the shutter/louver 140. Now when it is detected 206 that the trigger switch is off, the electromechanical control device 124 is controlled 208 to close the shutter/louver 140 and the above continues.

Figure 15:
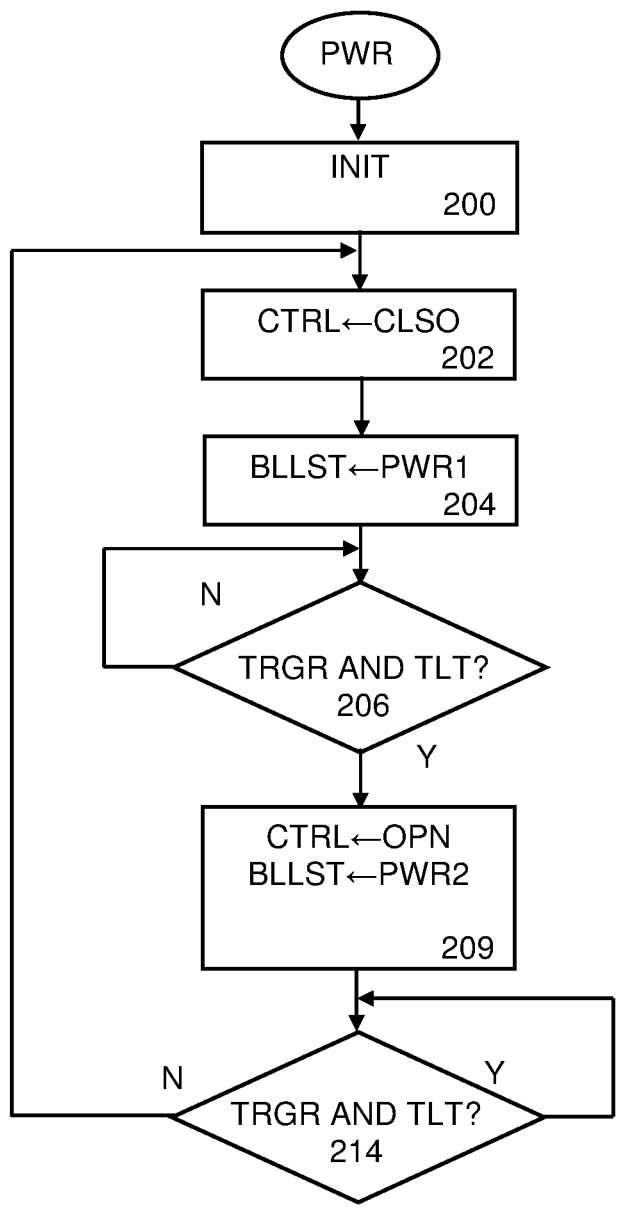
FIG. 15 illustrates a flow diagram of the handheld sanitization device having the optional tilt sensor and providing variable power to the ultraviolet emitters.

FIG. 15 shows a typical program flow of the handheld sanitization device with louvers/shutters 100 with the optional tilt sensor and providing variable power to the ultraviolet emitters. After initialization 200, the electromechanical control device 124 is controlled 202 to close the shutter/louver 140 and the ballast 127 is controlled 204 to power the ultraviolet emitters 110 with a first power level (e.g., a lower power level that maintains a low amount of ultraviolet emission). Now when it is detected 206 that the trigger switch is on and the optional tilt sensor 114 indicates proper orientation of the handheld sanitization device with louvers/shutters 100, the electromechanical control device 124 (e.g., any electromechanical device the imparts movement such as a solenoid, motor, servo motor, micromachine, etc.) is controlled 209 to open the shutter/louver 140 and the ballast 127 is controlled 204 to power the ultraviolet emitters 110 with a second power level (e.g., 100% power). Now, when it is detected 214 that the trigger switch is off or the optional tilt sensor 114 indicates improper orientation of the handheld sanitization device with louvers/shutters 100, the electromechanical control device 124 is controlled 202 to close the shutter/louver 140 and the above continues.

Figure 16:
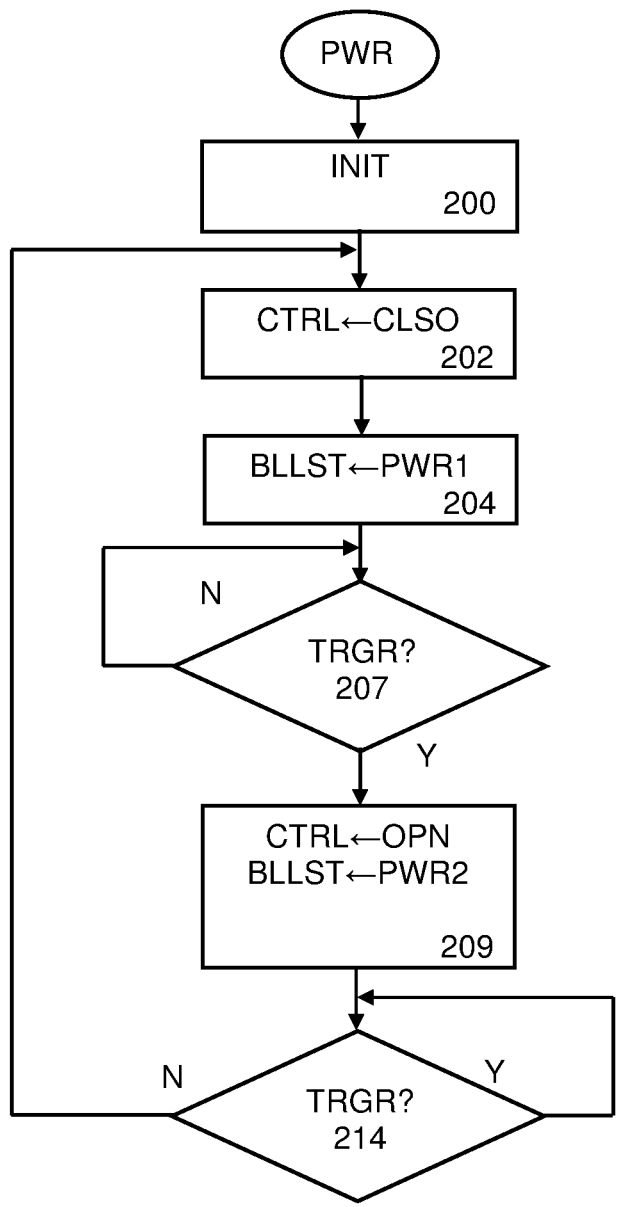
FIG. 16 illustrates a flow diagram of the handheld sanitization device without the optional tilt sensor and providing variable power to the ultraviolet emitters.

FIG. 16 shows a typical program flow of the handheld sanitization device with louvers/shutters 100 without the optional tilt sensor and providing variable power to the ultraviolet emitters. After initialization 200, the electromechanical control device 124 is controlled 202 to close the shutter/louver 140 and the ballast 127 is controlled to power the ultraviolet emitters 110 with a first power level (e.g., a lower power level that maintains a low amount of ultraviolet emission). Now when it is detected 207 that the trigger switch is on, the electromechanical control device 124 is controlled 209 to open the shutter/louver 140 and the ballast 127 is controlled to power the ultraviolet emitters 110 with a second power level (e.g., 100% power). Now, when it is detected 214 that the trigger switch is off, the electromechanical control device 124 is controlled 202 to close the shutter/louver 140 and the above continues.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

The invention claimed is:

1. A handheld sanitization device for sanitizing a surface using ultraviolet light and ozone, the handheld sanitization device comprising:
at least one ultraviolet emitter housed within an enclosure, the enclosure having a window for passing the ultraviolet light from the at least one ultraviolet emitter and onto the surface, the at least one ultraviolet emitter continuously powered to emit the ultraviolet light;
means for selectively blocking the window, the means for selectively blocking having an open position in which the ultraviolet light passes through the window and out of the enclosure and having a closed position in which the window is occluded, thereby blocking passage of the ultraviolet light from the at least one ultraviolet emitter, through the window and out of the enclosure, the means for selectively blocking is biased into the closed position;
an electromechanical device interfaced between the enclosure and the means for selectively blocking; and
a trigger switch electrically coupled to the electromechanical device, responsive to operation of the trigger switch, the means for selectively blocking is moved from the closed position into the open position by movement of the electromechanical device, thereby, releasing the ultraviolet light through the window.

2. The handheld sanitization device of claim 1, wherein responsive to abatement of the operation of the trigger switch, the means for selectively blocking is moved from the open position into the closed position by an opposing movement of the electromechanical device, thereby, blocking the ultraviolet light from escaping the enclosure through the window.

3. The handheld sanitization device of claim 1, wherein the means for selectively blocking is biased into the closed position by at least one spring.

4. The handheld sanitization device of claim 1, wherein the at least one ultraviolet emitter emits light in a 254 nm wavelength and in a 180 nm wavelength.

5. The handheld sanitization device of claim 1, wherein the window comprises a material selected from a group consisting of fused silica and fused quartz.

6. The handheld sanitization device of claim 1, further comprising a gravity sensor, the gravity sensor configured to inhibit operation of the electromechanical device unless the window is pointed in a downward direction towards earth, thereby the means for selectively blocking remains in the closed position until the window is pointed in the downward direction, thereby, blocking the ultraviolet light from escaping the enclosure through the window.

7. The handheld sanitization device of claim 1, wherein the trigger switch signals an electronic circuit within the enclosure such that the electronic circuit operates the at least one ultraviolet emitter at full power output in the open position and the electronic circuit operates the at least one ultraviolet emitter at less-than the full power output in the closed position.

8. A handheld sanitization device for sanitizing a surface using ultraviolet light and ozone, the handheld sanitization device comprising:
at least one ultraviolet emitter housed within an enclosure, the enclosure having a window for passing the ultraviolet light from the at least one ultraviolet emitter and onto the surface, the at least one ultraviolet emitter continuously powered to emit the ultraviolet light;
a louver, the louver positioned behind the window and having a fixed blocking section interfaced to the enclosure and having a movable blocking section slideably interfaced to the enclosure, the movable blocking section is movable between an open position in which the movable blocking section aligns with the fixed blocking section, thereby allowing the ultraviolet light to pass from the at least one ultraviolet emitter through the window and out of the enclosure and having a closed position in which fixed blocking section and the movable blocking section prevent the ultraviolet light from exiting the enclosure through the window, the movable blocking section is biased into the closed position;
an electromechanical device interfaced between the enclosure and the movable blocking section; and
a trigger switch electrically coupled to the electromechanical device, responsive to operation of the trigger switch, the movable blocking section is moved from the closed position into the open position by movement of the electromechanical device, thereby, releasing the ultraviolet light through the window.

9. The handheld sanitization device of claim 8, wherein responsive to abatement of the operation of the trigger switch, the movable blocking section is moved from the open position into the closed position by an opposing movement of the electromechanical device, thereby, blocking the ultraviolet light from escaping the enclosure through the window.

10. The handheld sanitization device of claim 8, wherein the at least one ultraviolet emitter emits light in a 254 nm wavelength and in a 180 nm wavelength.

11. The handheld sanitization device of claim 8, wherein the window comprises a material selected from a group consisting of fused silica and fused quartz.

12. The handheld sanitization device of claim 8, further comprising a gravity sensor, the gravity sensor configured to inhibit the electromechanical device unless the window is pointed in a downward direction towards earth, thereby the movable blocking section remains in the closed position until the window is pointed in the downward direction, thereby, blocking the ultraviolet light from escaping the enclosure through the window.

13. The handheld sanitization device of claim 8, wherein the trigger switch signals an electronic circuit within the enclosure such that the electronic circuit operates the at least one ultraviolet emitter at full power output in the open position and the electronic circuit operates the at least one ultraviolet emitter at less-than the full power output in the closed position.

14. A handheld sanitization device for sanitizing a surface using ultraviolet light and ozone, the handheld sanitization device comprising:
   at least one ultraviolet emitter housed within an enclosure, the enclosure having a window for passing the ultraviolet light from the at least one ultraviolet emitter and onto the surface, the at least one ultraviolet emitter continuously powered to emit the ultraviolet light;
   at least one shutter, the at least one shutter positioned behind the window and the at least one shutter are rotatably interfaced to the enclosure, the at least one shutter rotates between an open position in which each of the at least one shutter are at an angle of between 75 and 115 degrees with respect to the window, thereby allowing the ultraviolet light to pass from the at least one ultraviolet emitter through the window and out of the enclosure and the at least one shutter having a closed position in which each of the at least one shutter is parallel with or at a second angle of less than 10 degrees with respect to the window, thereby preventing the ultraviolet light from exiting the enclosure through the window, the at least one shutter is biased into the closed position;
   an electromechanical device interfaced between the enclosure and each of the at least one shutter; and
   a trigger switch electrically coupled to the electromechanical device, responsive to operation of the trigger switch, each of the at least one shutter is rotated from the closed position into the open position by movement of the electromechanical device, thereby, the ultraviolet light passes through the window.

15. The handheld sanitization device of claim 14, wherein responsive to abatement of operation of the trigger switch, each of the at least one shutter is moved from the open position into the closed position by an opposing movement of the electromechanical device, thereby, blocking the ultraviolet light from escaping the enclosure through the window.

16. The handheld sanitization device of claim 14, wherein the at least one ultraviolet emitter emits light in a 254 nm wavelength and in a 180 nm wavelength.

17. The handheld sanitization device of claim 14, wherein the window comprises a material selected from a group consisting of fused silica and fused quartz.

18. The handheld sanitization device of claim 14, further comprising a gravity sensor, the gravity sensor configured to inhibit the electromechanical device unless the window is pointed in a downward direction towards earth, thereby the at least one shutter remains in the closed position until the window is pointed in the downward direction, thereby, blocking the ultraviolet light from escaping the enclosure through the window until the window is pointed in the downward direction.

19. The handheld sanitization device of claim 14, wherein the trigger switch signals an electronic circuit within the enclosure such that the electronic circuit operates the at least one ultraviolet emitter at full power output in the open position and the electronic circuit operates the at least one ultraviolet emitter at less-than the full power output in the closed position.

20. The handheld sanitization device of claim 14, wherein each of the at least one shutter is biased into the closed position by at least one spring.

* * * * *